US006542575B1

(12) United States Patent
Schubert et al.

(10) Patent No.: US 6,542,575 B1
(45) Date of Patent: Apr. 1, 2003

(54) CORRECTION METHODS AND APPARATUS FOR DIGITAL X-RAY IMAGING

(75) Inventors: Scott Schubert, Delafield, WI (US); Ping Xue, Waukesha, WI (US)

(73) Assignee: General Electric Company, Schenectady, NY (US)

( * ) Notice: Subject to any disclaimer, the term of this patent is extended or adjusted under 35 U.S.C. 154(b) by 0 days.

(21) Appl. No.: 09/386,701

(22) Filed: Aug. 31, 1999

(51) Int. Cl.$^7$ ................................................. H05G 1/64

(52) U.S. Cl. ...................................... 378/98.4; 378/98.2

(58) Field of Search .............................. 378/98.4, 98.2

(56) References Cited

U.S. PATENT DOCUMENTS

| | | | | |
|---|---|---|---|---|
| 4,789,930 A | | 12/1988 | Sones et al. ............ | 364/413.13 |
| 4,829,552 A | | 5/1989 | Rossi et al. ................. | 378/154 |
| 4,875,227 A | | 10/1989 | Rossi et al. ................. | 378/154 |
| 5,050,198 A | * | 9/1991 | Honda ....................... | 378/98.4 |
| 5,195,120 A | | 3/1993 | Evain et al. ................ | 378/154 |
| 5,291,539 A | | 3/1994 | Thumann et al. ........... | 378/154 |
| 5,581,592 A | | 12/1996 | Zarnoch et al. ............ | 378/154 |
| 5,778,044 A | * | 7/1998 | Bruijns ..................... | 378/98.8 |

OTHER PUBLICATIONS

Barski, L.L., et al., "Characterization, Detection, and Suppersion of Stationary Grids in Digital Projection Radiography Imagery", *Proceedings of SPIE, Medical Imaging 1999, Image Display* (3658–59), 502–519, (1999).

* cited by examiner

Primary Examiner—Craig E. Church
(74) Attorney, Agent, or Firm—Schwegman, Lundberg, Woessner & Kluth, P.A.

(57) ABSTRACT

In recent years, x-ray imaging, which has been used to diagnose millions of illnesses and injuries, has evolved to use digital imaging instead of photographic film as a recording medium. Digital x-ray systems typically include an x-ray source, an x-ray focusing grid, and an array of light or x-ray detectors. Because of detector imperfections and other system factors, such as x-ray field non-uniformity and grid artifacts, digital x-ray images are often corrected, or compensated, before use. To this end, many digital x-ray systems include numerous application-specific correction maps, which unfortunately require regular maintenance that is not only time-consuming but expensive in terms of system downtime. Accordingly, the inventors devised new methods and systems for correcting application images that require maintenance of fewer correction maps. One exemplary implementation determines grid-only and non-grid correction maps and corrects application images based on a combination of these correction maps. Other aspects of the invention include automatic detection and correction of grid images in application images and computer-readable mediums which store software for computing and applying grid-only and non-grid correction maps.

27 Claims, 3 Drawing Sheets

CORRECTION METHODS AND APPARATUS FOR DIGITAL X-RAY IMAGING

TECHNICAL FIELD

The present invention concerns x-ray imaging, particularly methods of correcting digital x-ray images.

BACKGROUND OF THE INVENTION

Since its discovery in 1885, x-ray imaging has been used to successfully diagnose the illnesses and injuries of millions of people. This form of imaging generally entails passing x-rays, a form of high-energy radiation, through a body of material onto a phosphor plate. The phosphor plate glows, or luminesces, with an intensity dependent on the material the x-rays pass through. For example, x-rays that pass through bone produce a lower intensity glow than x-rays that pass through muscle. A photographic film next to the phosphor plate chemically reacts to the glow, making a two-dimensional record of its various intensities.

In recent years, x-ray imaging systems have gone "digital," essentially replacing photographic film with electronic imaging arrays. A typical digital x-ray system includes an x-ray source, an x-ray focusing grid, and an x-ray or light detector consisting of an array of pixels. The x-ray source emits x-rays, or photons, of a specific energy level in a narrow spray pattern through a body and toward the detectors. After passing through the body, the spray pattern includes primary and scattered photons. The x-ray focusing grid, placed between the body and the detector, absorbs most scattered photons and passes most primary photons onto the array of detector pixels.

In response, each detector pixel in the array provides an electrical output signal representative of the intensity of light or x-rays striking it. Each output signal is then converted to a number known as a digital pixel value, which is in turn output as a particular color on an electronic display or printing device, enabling viewing of the x-ray image.

Before display, it is common to correct the x-ray image for irregularities in the array of detectors. These irregularities, stemming from the uniqueness of each detector pixel in the array, lead the detector to output different signals in response to the same incident light or x-rays. Correcting the image typically entails adjusting the digital representation of each detector output signal by an experimentally determined number for that detector. The numbers for all the detector pixels, known collectively as a correction map, are usually stored in a digital memory of the x-ray system.

In addition to correcting for detector irregularities, the correction map also corrects for all other system sensitivity factors, such as non-uniform x-ray field and grid artifacts, affecting formation of a particular x-ray image. Because of the complex interdependency of the many factors affecting system sensitivity, every correction map is uniquely applicable to a specific system configuration and exposure technique, that is, to a specific set of system factors. Moreover, configuration and technique changes—such as increasing or decreasing x-ray tube voltage (kVp) and x-ray beam filter, or replacing one grid with another—that are made to tailor the system to specific imaging applications require use of different correction maps. Skulls, chests, and hands, for example, generally require different exposure techniques and grid types and thus different correction maps for best results.

Therefore, to support a wide variety of system configurations, digital x-ray imaging systems may store and use many application-specific correction maps. For example, if a system supports N different configurations and exposure techniques and P different grid options, it may store N×P (N times P) different correction maps to correct images made under all possible grid-and-technique combinations.

One problem with storing many application-specific correction maps is that they all require repeated maintenance or update to adjust for wear, age, and other time-varying characteristics of components in host x-ray systems. Updating, or recalibration, of many correction maps is not only time-consuming but expensive in terms of system downtime. Moreover, new x-ray applications and grid types are continually being developed, further expanding the number of correction maps requiring storage and update. Accordingly, there is a need for better correction methods and systems.

SUMMARY OF THE INVENTION

To address this and other needs, the inventors devised new methods and apparatus for correcting images in digital x-ray imaging systems. In systems which, for example, support N different non-grid configurations and P different grids and thus would conventionally require storage and update of N×P (N times P) different correction maps, these exemplary methods and apparatus in accord with the invention facilitate the same correction capability with storage of only N+P (N plus P) different correction maps. With storage of fewer correction map, systems incorporating various embodiments of the invention, ultimately require considerably less time and expense for recalibration.

One exemplary method determines grid-only and non-grid correction maps and corrects images based on a combinations of these "partial" or "modular" correction maps. More particularly, this exemplary method determines a grid-only correction map from first and second flat-field images, the first made without a grid and the second with a grid. The first image is used to determine the non-grid correction map, and both images are used to determine the grid-only correction map.

The exemplary apparatus includes a memory which stores one or more non-grid correction maps and one or more grid-only correction maps. Also included is software for selecting one or more of the non-grid correction maps and one of the grid-only correction maps and for correcting a given image using the selected non-grid and grid-only correction maps.

DESCRIPTION OF THE PREFERRED EMBODIMENTS

Figure 1:
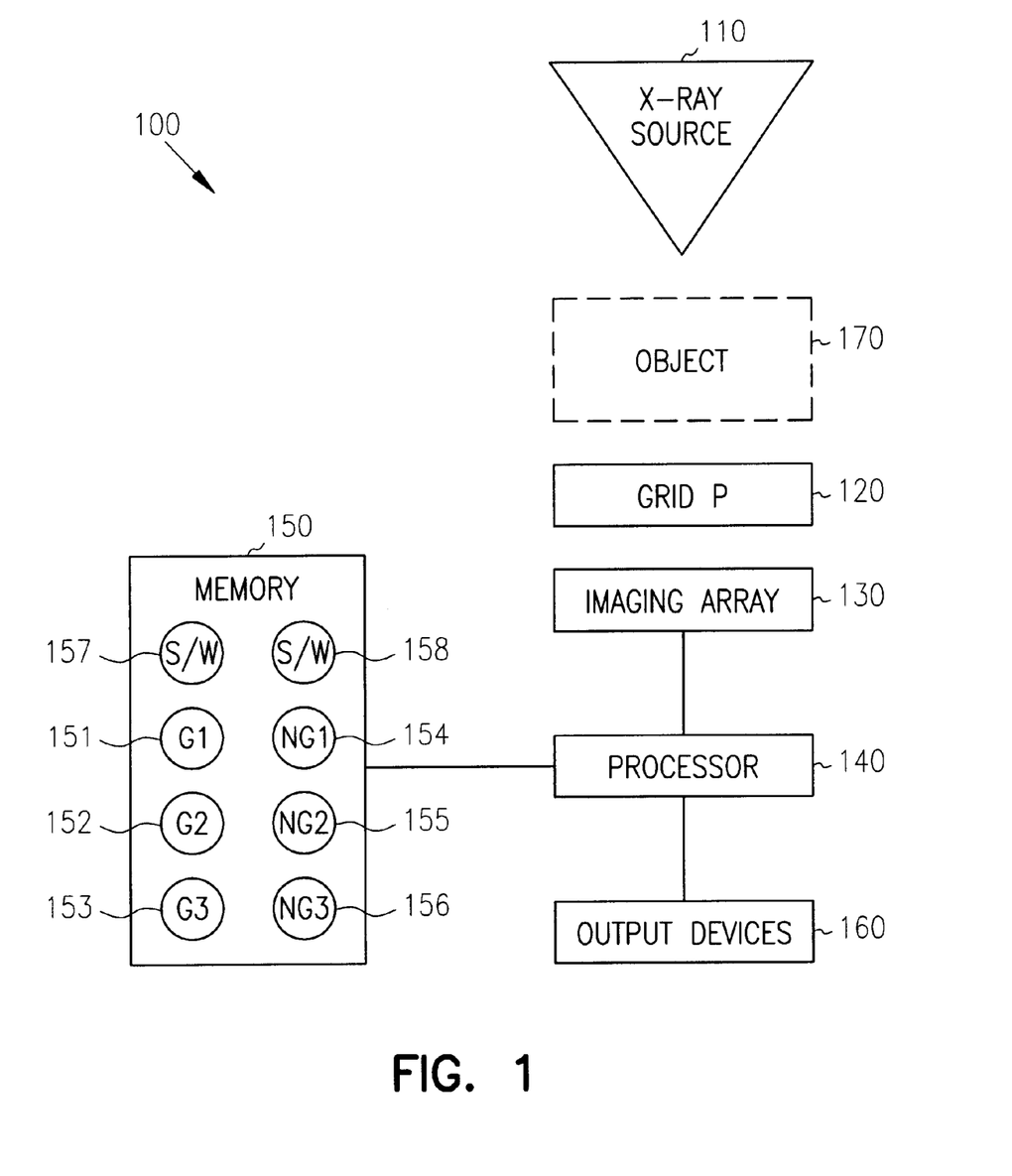
FIG. 1 is a block diagram of an exemplary digital x-ray imaging system 100 incorporating teachings of the present invention.
Figure 2:
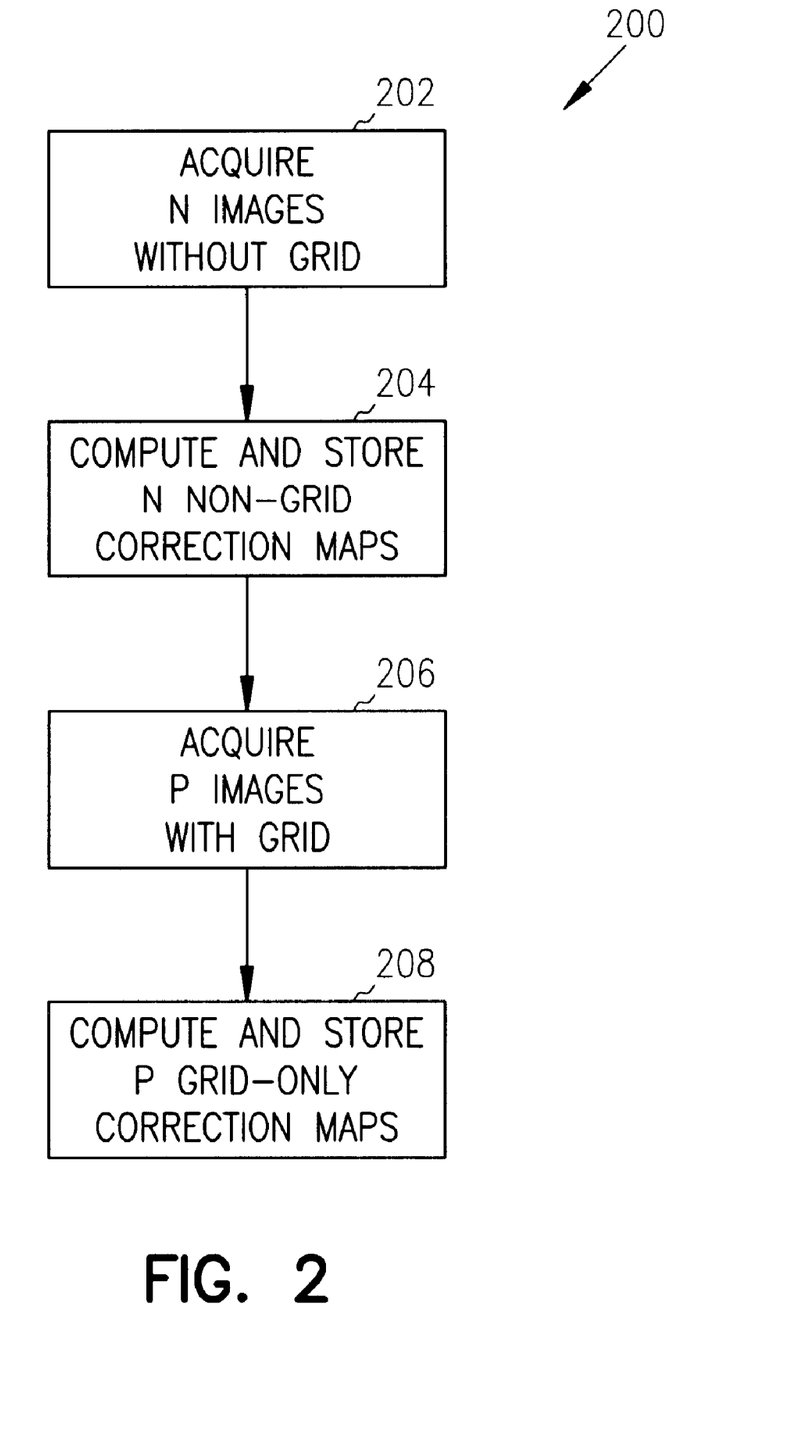
FIG. 2 is a flowchart 200 illustrating an exemplary method of determining grid-only and non-grid correction map, which also incorporates teachings of the present invention.
Figure 3:
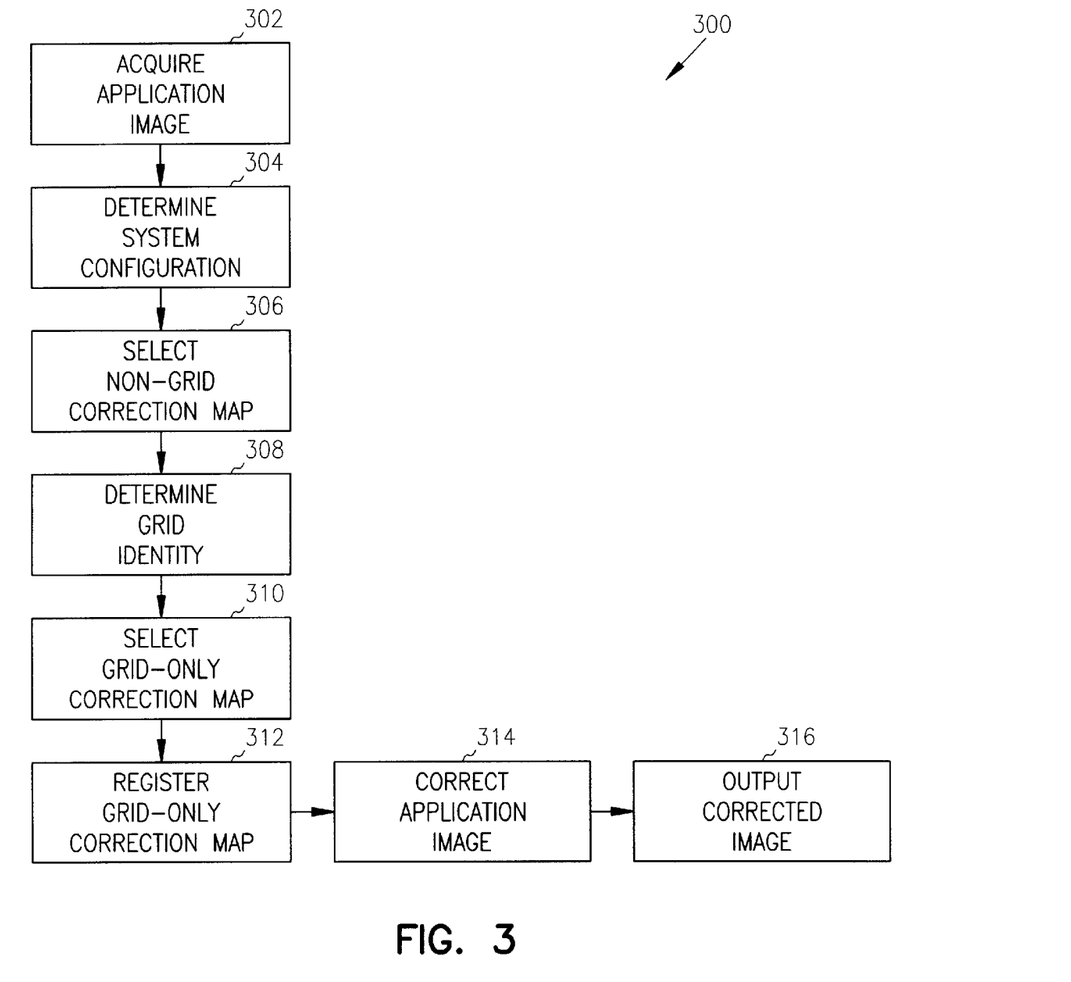
FIG. 3 is a flowchart 300 illustrating an exemplary method of correcting images, which also incorporates teachings of the present invention.

The following detailed description, which references and incorporates FIGS. 1–3, describes and illustrates one or more specific embodiments of the invention. These embodiments, offered not to limit but only to exemplify and teach the invention, are shown and described in sufficient detail to enable those skilled in the art to practice the invention. Thus, where appropriate to avoid obscuring the invention, the description may omit certain information known to those of skill in the art.

FIG. 1 shows an exemplary digital x-ray system 100 incorporating teachings of the present invention. In particular, system 100 includes an x-ray source 110, an x-ray focusing grid 120, an imaging array 130, a processor 140, a memory 150, and output devices 160. For clarity, other x-ray system components such as a collimator, system controller, automatic exposure controller, and so forth are not shown.

X-ray source 110 emits x-ray photons at one or more selectable energy levels. The exemplary embodiment uses any type of x-ray source, for example one with many different intensity settings. (The invention, however, is not limited to any type of x-ray source or any type, range, or number of selectable x-ray source operational criteria.) An object or body 170 placed between x-ray source 110 and x-ray focusing grid 120 absorbs, passes, and scatters x-ray photons based on its structure and composition.

X-ray focusing grid 120 absorbs most scattered photons and passes most primary photons onto imaging array 130. Grid 120, in the exemplary embodiment, is manually or automatically movable in and out of the path of radiation from x-ray source 110. Examples of suitable grids include those described in U.S. Pat. Nos. 5,581,592 and 5,291,539, which are incorporated herein by reference. Some embodiments use a focusing grid which carries strategic markers for locating it in x-ray images, and others include not only strategic markers, but also identification markers. The exemplary embodiment uses one of a number of grids P, generally denoted as grid 1, grid 2, ... , grid P. These are generically indicated as grid P in FIG. 1. (With adjustable or reconfigurable grids, each possible reconfiguration constitutes a separate grid P.) Primary photons that pass through grid 120 strike imaging array 130.

Imaging array 130 includes a two-dimensional array of sensors or detectors (not shown). In the exemplary embodiment, the array is rectangular and includes K rows and L columns of detectors, with each detector (or detector pixel) having a unique address or position based on its row and column. Though not shown, imaging array 130 also includes associated signal-conditioning electronics, such as sense amplifiers and/or analog-to-digital converters, as known or will be known in the art. In some embodiments, the detectors detect x-rays indirectly through light from a phosphor medium, and in others, the detectors detect x-rays directly. In either case, image array 130 provides a set of digital image signals, or pixel values, based on the output of the detectors to processor 140. (As used herein, image refers to a set of one or more pixel values originating, or otherwise derived through processing signals, from at least one corresponding detector in an imaging array.)

Processor 140 interfaces with memory 150 and output devices 160. Memory 150 includes a number of partial or modular correction maps 151–156. Partial correction maps 151, 152, and 153 are grid-only correction maps, that is, they are intended only to correct for grid effects in object, or application, images. On the other hand, partial correction maps 154, 155, and 156 are non-grid-correction maps, which are intended to correct the effects of one or more other system components on application images. (As used herein, map refers to array of numerical values intended for correction of an image.)

In the exemplary embodiment, the non-grid-correction maps correct for all other system components except for grids. However, in other embodiments, a number of distinct non-grid-correction maps correct independently for non-uniform x-ray field, x-ray beam geometry, or any other characteristics. Memory 150 also includes one or more software modules or computer programs 157 and 158 which respectively govern how processor 140 defines and applies each of the non-grid and grid-only correction maps. Exemplary memory devices include magnetic, optical, and electronic read-only memories, random-access-memories, and combinations of these types of devices.

Output devices 160 include one more image displays, printers, and/or communications devices for outputting image information. The communications devices allow transmission of image information over telephone and broadcast communications channels as desired to facilitate remote processing or diagnosis.

Generally, in normal operation after computing and storing one or more sets of partial-correction maps 151–156 and acquiring an application (object or patient) image, processor 140 determines identity of grid 120 by locating grid-identifying markers in the application image, by looking at operator inputs or settings, or by using Fourier transforms of the grid image and the application image. After this determination, processor 140 selects from memory 140 the appropriate combination of two or more partial-correction maps, for example, one grid-only correction map and at least one non-grid correction map, for use in correcting the application image. The processor then registers the correction maps to the application image and corrects the application image by applying the registered partial-correction maps sequentially to the application image. Alternatively, the processor mathematically combines the selected partial-correction maps into a total-correction map and then applies the total-correction map to the application image. The corrected application image is subject to further processing (not described here) and then transferred to output devices 160 for output in one or more desired forms.

FIGS. 2 and 3 respectively illustrate flow charts for exemplary methods of determining partial correction maps and then applying them to correct an application image. More particularly, FIG. 2 shows an exemplary flow chart 200, illustrating operation of system 100 and especially processor 140 in accord with software modules or computer programs 157. Flow chart 200 includes blocks 202–208, which are executed serially or in parallel in the exemplary embodiment. Some embodiments organize the exemplary process using a greater or lesser number of blocks. Other embodiments implement the blocks as two or more specific interconnected hardware modules with related control and data signals communicated between and through the modules. Thus, the exemplary process flow is applicable to software, firmware, and hardware implementations. In most, if not all instances, the process sequence can be varied from the order shown and described.

In addition to an assumption that grid effects and non-grid effects can be corrected separately, the exemplary process makes two basic assumptions about image data from imaging array 130. First, the exemplary process assumes that each detector pixel output signal $Y_{IJ}$ can be modeled as $$Y_{IJ}=M_{IJ}*X_{IJ}+OFF_I, \quad\quad\quad \text{Eq. (1)}$$

where subscript IJ generally denotes quantities derived from or related to the detector in the I-th row and the J-th column of the array of detectors; $M_{IJ}$ is the total sensitivity or gain of the detection system at detector pixel IJ; $X_{IJ}$ is the x-ray exposure at detector IJ in Roentgens; and $OFF_{IJ}$, is the offset, that is, the measured output at detector IJ without x-ray exposure. And second, it assumes that the total sensitivity $M_{IJ}$ can be modeled as $$M_{IJ} = f(G_{IJ}, NG_{IJ}), \qquad \text{Eq. (2)}$$

where f denotes a generic functional or mathematical combination; $G_{IJ}$ denotes a grid-only correction pixel value for detector IJ; and $NG_{IJ}$ denotes a non-grid-correction pixel value used for correcting the output of detector IJ for one or more non-grid effects. With these assumptions, the exemplary method proceeds as indicated in process blocks 202–208.

Process block 202 entails acquiring N first flat-field images without an object or patient and without x-ray focusing grid 120 being between x-ray source 110 and imaging array 130. Each of the N first flat-field images corresponds to a particular one of the N possible non-grid configurations of system 100. Prior to acquiring the first image, some embodiments manually or automatically move grid 120 out of the path of radiation from x-ray source 110. In some embodiments, a series of flat-field images are aggregated (with uniform or non-uniform weighting) and averaged to determine each of the N first flat-field images. Averaging the series of flat-field images reduces noise.

Each first flat-field image includes a set of K×L pixel values $Y1_n$ from imaging array 120, with individual pixel values denoted $Y1_{IJ,\,n}$, where I and J denote particular row and column indices and subscript n ranges from 1 to N, denoting the particular one of the N possible non-grid configurations associated with the first flat-field image. The exemplary embodiment models these pixel values as $$Y1_{IJ,\,n} = M'_{IJ,\,n} * X1_{IJ,\,n} + OFF1_{IJ,\,n} \qquad \text{Eq. (3a)}$$

where $Y1_{IJ,\,n}$ denotes the pixel value for the first image at detector IJ; $M'_{IJ,\,n}$ denotes the sensitivity for the detection system at detector pixel IJ in the no-grid configuration; $X1_{IJ,\,n}$ denotes the incident x-ray exposure at detector IJ; and $OFF1_{IJ,\,n}$, that is, the detector offset determined immediately before or after acquisition of the first image.

After acquiring the N first flat-field images, the exemplary process proceeds to block 204 to compute and store N non-grid correction maps $NG_1, NG_2, \ldots NG_N$ to memory 150. In the exemplary embodiment, computing the N non-grid correction maps entails adjusting each of the N first flat-field images for the offsets of each detector. Equation (3b) shows each pixel value in each non-grid correction map $NG_n$ is defined as $$NG_{IJ,\,n} = M'_{IJ,\,n} * X1_{IJ,\,n} = Y1_{IJ,\,n} - OFF1_{IJ,\,n} \qquad \text{Eq. (3b)}$$

Some embodiments of the invention normalize each of the non-grid correction maps before storing them to memory. One such embodiment normalizes each pixel value based on its mean value determined from a number of aggregated flat-field images. However, some embodiments normalize based on other measures of central tendency, based on an absolute or relative quantity for all the pixel values, or based on local or regional normalization techniques. The invention, however, is not limited to any particular normalization technique.

Execution then proceeds to process block 206, which entails acquiring P secong flat-field images without an object and with one of the P possible x-ray focusing grids 120 being between x-ray source 110 and imaging array 120. Each second flat-field image comprises a set of pixel values $Y2_p$, with subscript p denoting a particular one of the P possible x-ray focusing grids and with individual pixel values denoted $Y2_{IJ,\,p}$. The exemplary embodiment models these pixel values as $$Y2_{IJ,\,p} = M_{IJ,\,p} * X2_{IJ,\,p} + OFF2_{IJ,\,p}, \qquad \text{Eq. (4)}$$

where $Y2_{IJ,\,p}$ denotes the pixel value for thye second image at detector IJ; $M_{IJ,\,p}$ denotes the total sensitivity of the detection system at detector pixel IJ with grid p in place; $X2_{IJ,\,p}$ denotes the incident x-ray exposure at detector IJ for the second image; and $OFF2_{IJ,\,p}$ denotes the detector offset determined immediately before or after acquisition of the second flat-field image. In some embodiments, a series of images of each grid p are aggregated (using uniform of non-uniform weighting) and averaged to determine each of the P second flat-field images.

$$Y3_{IJ,\,np} = M_{IJ,\,np} * X3_{IJ,\,np} + OFF3_{IJ,\,np} \qquad \text{Eq. (6)}$$

After acquiring the P second flat-field images, the processor proceeds to block 208 where it computes and stores P grid-only correction maps $G_1, G_2, \ldots G_P$ to memory 150. If the first and second flat-field images are acquired with sufficiently low noise and approximately equal radiation exposures, that is, $X1_{IJ}$ approximately equals $X2_{IJ}$, then the pixel values for each grid-only correction map can be calculated as $$G_{IJ,\,p} = [Y2_{IJ,\,p} - OFF2_{IJ}] * [NG_{IJ,\,n}]^{-1} \qquad \text{Eq. (5a)}$$

where $NG_{IJ,\,n}$ is defined in equation (3b) and where p denotes the particular grid and n denotes the system configuration used in acquiring the associated second flat-field image. Equation (5a) represents the proposition that the grid-only correction map can be calculated from a flat-field image of the grid that is itself corrected by the flat-field image without the grid.

In embodiments that normalize the flat-field images (or quantities based on these images), there is no restriction on the relation of the radiation exposure levels $X1_{IJ}$ and $X2^{IJ}$. In this case, the pixel values for each grid-only correction map can be calculated as $$G_{IJ,\,p} = Norm[Y2_{IJ,\,p} - OFF2_{IJ,\,p} * \{Norm'[NG_{IJ,\,n}]\}^{-1} \qquad \text{Eq. (5b)}$$

where Norm and Norm' denote respective normalization functions or techniques. In some embodiments, Norm and Norm' are the same, and in other embodiments they are different.

After being computed and stored in memory 150, the partial-correction maps are ready to be used to correct appropriate application images. (Note that these partial correction maps are subject to regular updates using the method outlined in FIG. 2, thereby ensuring that the maps reflect a reasonably current state of the x-ray system.) In some embodiments, there is substantial delay—for example, hours, days, weeks, or months—between computation and storage of the partial-correction maps and their actual use in correcting application images as shown in FIG. 3.

FIG. 3 shows an exemplary flow chart 300, illustrating operation of system 100 and especially processor 140 in accord with software modules or computer programs 158. Like flow chart 200, flow chart 300 is applicable to software, firmware, and hardware implementations. Flow chart 300 includes process blocks 302–316, which can be executed serially or in parallel or reorganized as a greater or lesser number of blocks. In most, if not all instances, the process sequence can be varied from the order shown and described.

In process block 302, system 100 acquires an application (patient or object) image with one of N possible system configurations and techniques defined by one or more non-grid operating criteria, such as tube and detector position, and one of P possible x-ray focusing grids placed between the x-ray source and the imaging array. Other non-grid operating criteria which some embodiments use to define system configurations and techniques include x-ray beam energy spectrum, kVp and beam filtration, x-ray beam spatial variation, source-to-image distance, x-ray collimation, x-ray tube focal spot, ion chamber characteristics, and tube, grid, and detector array alignment.

The application image comprises a set of pixel values $Y3_{np}$, with n denoting the particular non-grid system configuration and p denoting the particular grid used in forming the application image. Each pixel value $Y3_{IJ,\ np}$ has the form:

$$Y3_{IJ,\ np} = M_{IJ,\ np} * X3_{IJ,\ np} + OFF3_{IJ,\ np} \qquad \text{Eq. (6)}$$

where $Y3_{IJ,\ np}$ denotes the uncorrected pixel value for the application image at detector IJ; $M_{IJ,\ np}$ denotes the total sensitivity of the detection system at detector pixel IJ with non-grid configuration n and grid p; $X3_{IJ,\ np}$ denotes the incident x-ray exposure at detector IJ for the application image; and $OFF3_{IJ,\ np}$ denotes the detector offset immediately before or after acquisition of the application image. After adjusting for offset, each pixel value of the application image has the form $M_{IJ,\ np} * X3_{IJ,\ np}$.

In block 304, the processor determines the non-grid system configuration used for the application image. In the exemplary embodiment, this entails examining one or more operator inputs or corresponding x-ray system settings. Some embodiments determine the non-grid system configuration through identification of two or more parameters such as tube voltage, kVp, and focal-spot specification.

In block 306, the processor uses its determination of the non-grid system configuration to select one or more non-grid correction maps from memory. In the exemplary embodiment, this entails choosing an existing non-grid correction map which was generated for the non-grid system configuration used to form the subject application image. However, in other embodiments, this entails selecting two or more non-grid correction maps, each one addressing a different non-grid aspect of the system configuration. After selecting one or more appropriate non-grid correction maps, execution of the exemplary method continues at block 308.

Block 308 entails determining the identity or type of grid placed between the x-ray source and the imaging array and finding the identified in the application image. There are at least three ways to determine grid identity or type and to find the grid. A first method is to look at x-ray system inputs or settings indicating the grid identity or type. A second method is to recognize identity or type markers from the grid in the application image. And, a third is to compare the distinct Fourier transforms of each of the possible grids to Fourier transforms of the application image, using signature spectrum features for discrimination. Finding the grid includes determining the rotation and translation of the identified grid in the application image.

The exemplary process then executes blocks 310 and 312. Block 310 entails using the determined grid identity or grid type to select a grid-only correction map, such as grid-only correction map P, from memory. And block 312 entails registering the selected grid-only correction map to the application image. Registration entails orienting the grid-only correction map to the application image to ensure that its pixel correction values are applied to the correct pixels of the application image. The exemplary embodiment uses affine registration, Fourier spectrum analysis, or the location of visible grid features in the application image to ensure proper registration.

Block 314 entails correcting the application image based on the one or more selected non-grid correction maps and the selected grid-only correction map. In the exemplary embodiment, this entails applying partial correction maps $G_p$ and $NG_n$ to the application image as prescribed in equation (7):

$$Y3'_{IJ} = [f(G_{IJ,\ p}, NG_{IJ,\ n})]^{-1} * [Y3_{IJ,\ np} - OFF3_{IJ,\ np}], \qquad \text{Eq. (7)}$$

where $Y3'_{IJ}$ denotes the corrected pixel value for pixel value IJ of the application image; $f(G_{IJ}, NG_{IJ})]^{-1}$ denotes the total correction map as defined in equation (2); and the quantity $[Y3_{IJ} - OFF3_{IJ}]$ denotes the offset corrected application image pixel value IJ. In implementing equation (7), the exemplary embodiment defines $f(G_{IJ,\ p}, NG_{IJ,\ n})$ as the product of $G_{IJ}$ and $NG_{IJ}$, or $$f(G_{IJ,\ p}, NG_{IJ,\ n}) = G_{IJ,\ p} * NG_{IJ,\ n} \qquad \text{Eq. (8a)}$$

In embodiments that use normalized correction maps, $f(G_{IJ,\ p}, NG_{IJ,\ n})$ as the following form:

$$f(G_{IJ,\ p}, NG_{IJ,\ n}) = Norm[G_{IJ,\ p}] * Norm[NG_{IJ,\ n}] \qquad \text{Eq. (8b)}$$

After correcting the application image as indicated in equation (7), the exemplary method executes block 316. Block 316 entails outputting the corrected image to output devices 160.

CONCLUSION

In furtherance of the art, the inventors devised new methods and apparatus using non-grid and grid-only correction maps for correcting application images in direct and indirect digital imaging systems. In systems which, for example, support N different non-grid configurations and P different grids and thus would conventionally require storage and update of N×P (N times P) different correction maps, exemplary methods and apparatus in accord with the invention facilitate the same correction capability with storage of only N+P (N plus P) different correction maps.

The embodiments described above are intended only to illustrate and teach one or more ways of practicing or implementing the present invention, not to restrict its breadth or scope. The actual scope of the invention, which embraces all ways of practicing or implementing the teachings of the invention, is defined only by the following claims and their equivalents.

What is claimed is:

1. A method of correcting application images in an x-ray system having one or more grids and one or more other components, the method comprising:

determining a grid-only correction map for correcting grid effects in application images;

determining a non-grid correction map for correcting application images only for non-grid effects based one or more of the other components, with the non-grid correction map based on transmission of x-rays within the system; and correcting an application image based on the grid-only and the non-grid correction maps.

2. The method of claim 1, wherein determining the grid-only correction map occurs after determining the non-grid correction map.

3. The method of claim 1 wherein determining a grid-only correction map comprises:
  acquiring a first image without a grid;
  acquiring a second image with a grid; and
  determining the grid-only correction map based on the first and second images.

4. A method of correcting application images in an x-ray system having one or more grids and one or more other components, the method comprising:
  determining a grid-only correction map for correcting grid effects in application images, wherein determining the grid-only correction map comprises:
    acquiring a first image without a grid;
    acquiring a second image with a grid; and
    determining the grid-only correction map based on the first and second images,
    wherein determining the grid-only correction map based on the first and second images comprises calculating one or more values of the grid-only correction map based on $$[Y2_{IJ}-OFF2_{IJ}]*[Y1_{IJ}-OFF1_{IJ}]^{-1}$$

where $Y1_{IJ}$ and $Y2^{IJ}$ are based on respective values from the first and second images and $OFF1_{IJ}$ and $OFF2_{IJ}$ are based on offsets for a detector;
  determining a non-grid correction map for correcting application images for effects based one or more of the other components; and
  correcting an application image based on the grid-only and the non-grid correction maps.

5. The method of claim 1 wherein the determined non-grid-correction map is based on at least one of x-ray beam energy spectrum, x-ray beam filtration, x-ray beam spatial variation, ion chamber characteristics, detector irregularities, and alignment of the x-ray system.

6. A method of correcting application images in an x-ray system having one or more grids and one or more other components, the method comprising:
  determining a grid-only correction map for correcting grid effects in application images;
  determining a non-grid correction map for correcting application images for effects based one or more of the other components; and
  correcting an application image based on the grid-only and the non-grid correction maps, wherein correcting an application image based on the grid-only and the non-grid correction maps comprises correcting one or more portions of the application image based on $$[f(G_{IJ}, NG_{IJ})]^{-1}*[Y_{IJ}-OFF_{IJ}],$$

where $f(G_{IJ}, NG_{IJ})$ denotes a function of the respective grid-only correction map and the non-grid-correction map; $Y_{IJ}$ denotes a value for a portion of the application image; and $OFF_{IJ}$ denotes a detector offset.

7. A method of correcting application images in an x-ray system having one or more grids and one or more other components, the method comprising:
  determining a grid-only correction map for correcting grid effects in application images;
  determining a non-grid correction map for correcting application images for effects based one or more of the other components; and
  correcting an application image based on the grid-only and the non-grid correction maps, wherein correcting an application image based on the grid-only and the non-grid correction maps comprises correcting one or more portions of the application image based on $$[f(G_{IJ}, NG_{IJ})]^{-1}*[Y_{IJ}-OFF_{IJ}],$$

where $f(G_{IJ}, NG_{IJ})$ denotes a function of the respective grid-only correction map and the non-grid-correction map; $Y_{IJ}$ denotes a value for a portion of the application image; and $OFF_{IJ}$ denotes a detector offset, wherein the function includes a product of corresponding portions of the grid-only correction map and the non-grid-correction map.

8. A method of correcting application images in an x-ray system having one or more grids and one or more other components, the method comprising:
  determining a grid-only correction map for correcting application images, wherein determining a grid-only correction map comprises:
    acquiring a first image without a grid and without an object;
    acquiring a second image with one of the grids and without an object; and calculating one or more values of the grid-only correction map based on $$[Y2_{IJ}-OFF2_{IJ}]*[Y1_{IJ}-OFF1_{IJ}]^{-1}$$

where $Y1_{IJ}$ and $Y2^{IJ}$ denote respective values from the first and second images and $OFF1_{IJ}$ and $OFF2_{IJ}$ denote respective offsets for a detector during respective acquisition of the first and second images;
  determining a non-grid-correction map for correcting application images for one or more of the other components; and
  correcting an application image based on the grid-only and the non-grid correction maps.

9. A method of correcting application images in an x-ray system having one or more grids and one or more other components, the method comprising:
  determining a grid-only correction map for correcting application images;
  determining a non-grid correction map for correcting application images for one or more of the other components; and
  correcting an application image based on the grid-only and the non-grid correction maps, wherein correcting the application image based on the grid-only and the non-grid correction maps comprises correcting one or more portions of the application image based on $$[f(G_{IJ}, NG_{IJ})]^{-1}*[Y_{IJ}-OFF_{IJ}],$$

where $f(G_{IJ}, NG_{IJ})$ denotes a function of the respective grid-only correction map and the non-grid-correction map; $Y_{IJ}$ denotes a value for a portion of the application image; and $OFF_{IJ}$ denotes a detector offset.

10. In an x-ray system having an x-ray source, an x-ray focusing grid, and an imaging array, a method of correcting application images, comprising:
  acquiring a first image without an object and without the x-ray focusing grid between the x-ray source and the imaging array, the first image comprising a first set of one or more pixel values from the imaging array;
  determining a non-grid-correction map from the first image for correcting only non-grid effects, the non-grid-correction map comprising a set of one or more pixel values based at least in part on transmission of x-rays within the system;

acquiring a second image without an object and with the x-ray focusing grid between the x-ray source and the image array, the second image comprising a second set of one or more pixel values from the imaging array;

determining a grid-only correction map based on the first and second sets of pixel values, the grid-only correction map comprising a set of one or more pixel values, with each pixel value of the grid-only correction map based on at least one of the first set of pixel values and at least one of the second set of pixel values;

acquiring a third image with an object and the x-ray focusing grid between the x-ray source and the imaging array, the third image comprising a third set of one or more pixel values from the imaging array; and determining one or more corrected pixel values from the third set of pixel values based on at least one pixel value of the set of pixel values of the grid-only correction map and one pixel value of the set of non-grid correction map.

11. A method of correcting application images in an x-ray system having one or more grids and one or more other components, the method comprising:

a step for determining a grid-only correction map for correcting application images;

a step for determining two or more non-grid-correction maps for correcting application images for one or more of the other components, with each non-grid correction map based on transmission of x-rays within the system; and a step for correcting an application image based on the grid-only correction map and at least one of the non-grid correction maps.

12. The method of claim 4, wherein the listed acts occur in the listed order.

13. The method of claim 4, wherein acquiring a first image without a grid comprises acquiring two or more images without a grid and acquiring a second image with a grid each comprise acquiring two or more images without a grid.

14. A method of operating a digital x-ray imaging system, comprising:

storing one or more grid-only correction maps, with each grid correction map based on transmission of x-rays within the system;

storing two or more non-grid correction maps, with each non-grid correction map based on transmission of x-rays within the system; and correcting an application image based on at least one of the grid-only correction maps and at least one of the non-grid correction maps.

15. A method of operating a digital x-ray imaging system, comprising:

storing two or more non-grid correction maps, with each non-grid correction map based on transmission of x-rays within the system; and correcting an application image based on at least one of the non-grid correction maps.

16. A modular method of correcting images in a digital x-ray imaging system having at least first and second components, the method comprising:

selecting a first partial-correction map from a first set of two or more partial-correction maps for correcting application images based on the first component, with the first partial-correction map based on transmission of x-rays within the system;

selecting a second partial-correction map from a second set of two or more partial-correction maps for correcting application images based on at least the second component and not on the first component, with the second partial-correction map based on transmission of x-rays within the system; and correcting an image based on at least the first and second partial-correction maps.

17. The modular method of claim 16:

wherein the first component is an x-ray focusing grid and the first partial-correction map corrects for the x-ray focusing grid; and wherein correcting the application image comprises determining at least one product based on respective values of at least one of the grid-only corrections and at least one of the non-grid correction maps.

18. A method of correcting images in a digital x-ray imaging system having at least first and second components, the method comprising:

selecting a first correction map from a first set of correction maps for use in correcting an image for effects based on the first component, with the first partial-correction map based on transmission of x-rays through the system;

selecting a second correction map from a second set of correction maps for use in correcting the image for effects based on at least the second component and not based on the first component, with the second partial-correction map based on transmission of x-rays within the system; and correcting an image based on the first and second correction maps.

19. The method of claim 18, wherein correcting an image comprises determining a plurality of products, with each product based on respective values of the first correction map and the second correction map.

20. The method of claim 1, wherein correcting the application image comprises determining a plurality of products, with each product based on respective values of the grid-only correction map and the non-grid correction map.

21. A digital x-ray imaging system for making and displaying application images, comprising:

means for generating x-rays;

means for acquiring an image;

one or more grid means for placement between the means for generating x-rays and the means for acquiring an image;

means for determining a grid-only correction map for correcting application images based on one or more of the grid means;

means for determining a non-grid-correction map for correcting application images based on characteristics of at least the means for generating x-rays and the means for acquiring an image;

means for correcting an application image based on the grid-only correction map and the non-grid correction map; and means for displaying the corrected application image.

22. A digital x-ray imaging system for making and displaying application images, comprising:

means for storing one or more grid-only correction maps;

means for storing two or more non-grid correction maps, with each non-grid correction map based on transmission of x-rays within the system; and means for selecting at least one of the grid-only correction maps and at least one of the non-grid correction maps for use in correcting an application image.

23. A digital x-ray imaging system for making and displaying application images, comprising:

means for storing one or more grid-only correction maps;

means for storing two or more non-grid correction maps, with each non-grid correction map based on transmission of x-rays within the system;

means for selecting at least one of the grid-only correction maps and one of the non-grid correction maps;

means for correcting an application image based on the selected grid-only correction map and the selected non-grid correction map; and means for displaying the corrected application image.

24. A digital x-ray imaging system for making and displaying application images, comprising:

means for generating x-rays;

means for acquiring an image;

one or more grid means for placement between the means for generating x-rays and the means for acquiring an image;

means for storing one or more grid-only correction maps and two or more non-grid correction maps, with each non-grid correction map based on generated x-rays;

means, responsive to one or more of the grid means, for selecting at least one of the grid-only correction maps;

means for selecting one of the non-grid correction maps;

means for correcting an application image based on the selected grid-only correction map and the selected non-grid correction map; and means for displaying the corrected application image.

25. A computer-readable medium comprising instructions for:

determining a grid-only correction map for correcting grid effects in application images from an imaging system;

determining a non-grid correction map for correcting application images for effects based one or more of non-grid components in the imaging system, with the non-grid correction map based on transmission of x-rays within the system; and correcting an application image based on the grid-only and the non-grid correction maps.

26. A computer-readable medium comprising:

means for determining a grid-only correction map for correcting grid effects in application images from an imaging system;

means for determining a non-grid correction map for correcting application images for effects based one or more of non-grid components in the imaging system, with the non-grid correction map based on energy incident to an imaging array in the system; and means for correcting an application image based on the grid-only and the non-grid correction maps.

27. A digital x-ray imaging system comprising:

means for selecting a grid-only correction map from a set of two or more grid-only correction maps for correcting application images based on grid effects;

means for selecting a non-grid-correction map from a set of two or more non-grid correction maps for correcting application images based on effects related to one or more of non-grid components, with each non-grid correction map based on transmission of x-rays within the system; and means for correcting an application image based on the grid-only and the non-grid correction maps.

* * * * *

UNITED STATES PATENT AND TRADEMARK OFFICE
CERTIFICATE OF CORRECTION

PATENT NO. : 6,542,575 B1
DATED : April 1, 2003
INVENTOR(S) : Scott Schubert and Ping Xue It is certified that error appears in the above-identified patent and that said Letters Patent is hereby corrected as shown below:

Column 5,
Line 64, delete "secong" and insert -- second -- therefor.

Column 6,
Line 7, delete "thye" and insert -- the -- therefor.
Line 18, delete "$Y3_{IJ, np}=M_{IJ, np} *X3_{IJ, np} +OFF3_{IJ, np}$     Eq. (6)".
Line 40, delete "$X2^{IJ}$" and insert -- $X2_{IJ}$ -- therefor.

Column 8,
Line 19, delete "$f(G_{IJ, p}, NG_{IJ, n})$" and insert -- $f(G_{IJ}, NG_{IJ})$ -- therefor.

Column 9,
Line 24, delete "$Y2^{IJ}$" and insert -- $Y2_{IJ}$ -- therefor.

Column 10,
Line 27, delete "$Y2^{IJ}$" and insert -- $Y2_{IJ}$ -- therefor.

Signed and Sealed this

Tenth Day of February, 2004

JON W. DUDAS
*Acting Director of the United States Patent and Trademark Office*